United States Patent
Glaser et al.

(10) Patent No.: US 9,706,950 B2
(45) Date of Patent: Jul. 18, 2017

(54) ACCELEROMETER AND WIRELESS NOTIFICATION SYSTEM

(71) Applicant: ANGULUS CORP., New York, NY (US)

(72) Inventors: Frank Glaser, New York, NY (US); Viktor Gamarnik, New York, NY (US); Daniel Karlin, Arlington, MA (US)

(73) Assignee: ANGULUS CORP., New York, NY (US)

( * ) Notice: Subject to any disclaimer, the term of this patent is extended or adjusted under 35 U.S.C. 154(b) by 0 days.

(21) Appl. No.: 14/675,105

(22) Filed: Mar. 31, 2015

(65) Prior Publication Data

US 2015/0272481 A1    Oct. 1, 2015

Related U.S. Application Data

(60) Provisional application No. 61/972,841, filed on Mar. 31, 2014.

(51) Int. Cl.
| | |
|---|---|
| *A61B 5/00* | (2006.01) |
| *A61B 5/11* | (2006.01) |
| *A61B 5/0205* | (2006.01) |
| *G06F 19/00* | (2011.01) |
| *A61B 5/107* | (2006.01) |

(Continued)

(52) U.S. Cl.
CPC .......... *A61B 5/1116* (2013.01); *A61B 5/0022* (2013.01); *A61B 5/0205* (2013.01); *G06F 19/3418* (2013.01); *A61B 5/01* (2013.01); *A61B 5/021* (2013.01); *A61B 5/024* (2013.01); *A61B 5/05* (2013.01); *A61B 5/0816* (2013.01); *A61B 5/1071* (2013.01); *A61B 5/1121* (2013.01); *A61B 5/1135* (2013.01); *A61B 5/14542* (2013.01); *A61B 5/6804* (2013.01); *A61B 5/742* (2013.01); *A61B 5/746* (2013.01); *A61B 2505/07* (2013.01); *A61B 2560/0475* (2013.01); *A61B 2562/0219* (2013.01); *G06F 19/3481* (2013.01)

(58) Field of Classification Search
CPC ........ A61B 5/1115; A61B 5/1116; A61B 5/11
See application file for complete search history.

(56) References Cited

U.S. PATENT DOCUMENTS

| | | |
|---|---|---|
| 5,593,431 A | 1/1997 | Sheldon |
| 6,937,900 B1 | 8/2005 | Pianca et al. |

(Continued)

FOREIGN PATENT DOCUMENTS

WO    WO 2013/173747 A1    11/2013

OTHER PUBLICATIONS

International search report and written opinion dated Jul. 1, 2015 for PCT Application No. PCT/US2015/023697.

(Continued)

*Primary Examiner* — Michael D Abreu
(74) *Attorney, Agent, or Firm* — Wilson Sonsini Goodrich & Rosati

(57) ABSTRACT

The present disclosure provides methods and devices for managing health conditions associated with posture. The devices can be configured to monitor patient body angles and alert caregivers when measurements are outside a recommended range for the health condition. The methods and devices can facilitate patient compliance and assist caregivers in adhering to action plans.

34 Claims, 10 Drawing Sheets

(51) Int. Cl.
| A61B 5/145 | (2006.01) |
| A61B 5/024 | (2006.01) |
| A61B 5/08 | (2006.01) |
| A61B 5/05 | (2006.01) |
| A61B 5/01 | (2006.01) |
| A61B 5/021 | (2006.01) |
| A61B 5/113 | (2006.01) |

(56) References Cited

U.S. PATENT DOCUMENTS

| 7,117,607 | B2 | 10/2006 | Horgan |
| 7,562,458 | B1 | 7/2009 | Clark, Jr. et al. |
| 8,063,785 | B2 | 11/2011 | Sacchetti |
| 8,519,852 | B2 | 8/2013 | Johnson et al. |
| 2003/0040776 | A1 | 2/2003 | Kroll et al. |
| 2011/0066007 | A1* | 3/2011 | Banet ............... A61B 5/0402 600/301 |
| 2012/0108915 | A1* | 5/2012 | Corbucci ........... A61B 5/02028 600/301 |
| 2012/0172681 | A1 | 7/2012 | Sun et al. |
| 2013/0085418 | A1 | 4/2013 | Salhani |

OTHER PUBLICATIONS

Akerman, et al. Clinical experience and incidence of ventilator-associated pneumonia using closed versus open suction-system. Nurs Crit Care. Jan. 2014;19(1):34-41.

Apostolopoulou, et al. Incidence and risk factors for ventilator-associated pneumonia in 4 multidisciplinary intensive care units in Athens, Greece. Respir Care. Jul. 2003;48(7):681-8.

Balonov, et al., A novel method of continuous measurement of head of bed elevation in ventilated patients.Intensive Care Med. Jun. 2007;33(6):1050-4.

Blot, et al., How toavoid microaspiration? A key element for the prevention of ventilator-associated pneumoniain intubated ICU patients. BMC Infectious Diseases. Nov. 28, 2014.

Croce, et al. National Trauma Institute prospective evaluation of the ventilator bundle in trauma patients: does it really work? J Trauma Acute Care Surg. Feb. 2013;74(2):354-60.

Curtis, et al. Intensive care unit quality improvement: a "how-to" guide for the interdisciplinary team. Crit Care Med. Jan. 2006;34(1):211-8.

Drakulovic, et al. Supine body position as a risk factor for nosocomial pneumonia in mechanically ventilated patients: a randomised trial. Lancet. Nov. 27, 1999;354(9193):1851-8.-body-position-as-a-risk-1999.

Eom, et al. The impact of a ventilator bundle on preventing ventilator-associated pneumonia: a multicenter study. Am J Infect Control. Jan. 2014;42(1):34-7.

Grap, et al. Predictors of backrest elevation in critical care. Intensive Crit Care Nurs. Apr. 2003;19(2):68-74.

Hamishekar, et al. Education alone is not enough in ventilator associated pneumonia care bundle compliance. Journal Res Pharm Pract. Apr. 2014;3(2):51-5.

Keyt, et al. Prevention of ventilator-associated pneumonia in the intensive care unit: A review of the clinically relevant recent advancements. Indian Journal Med Res. Jun. 2014;139(6): 814-821.

Kollef, et al. The Effect of Late-Onset: Ventilator-Associated Pneumonia in Determining Patient Mortality. American College of Chest Physicians. 1995;108(6):1655-1662.

Kollef, et al. Ventilator-associated pneumonia. A multivariate analysis. JAMA. Oct. 27, 1993;270(16):1965-70.

Liu, et al. Factors associated with low adherence to head-of-bed elevation during mechanical ventilation in Chinese intensive care units. Chin Med J (Engl). Mar. 2013;126(5):834-8.

Medscape. A Simple Device to Increase Rates of Compliance in Maintaining 30-Degree Head-of-bed Elevation in Ventilated Patients. Available at http://www.medscape.com/viewarticle/574911. Accessed on Oct. 10, 2016.

Nieuwenhoven, et al. Feasibility and effects of the semirecumbent position to prevent ventilator-associated pneumonia: a randomized study. Crit Care Med. Feb. 2006;34(2):396-402.

PA Patient Saf Advis. Successful Reduction of Ventilator-Associated Pneumonia. Available at http://patientsafetyauthority.org/ADVISORIES/AdvisoryLibrary/2009/Jun6(2)/Pages/63.aspx. Accessed on Oct. 10, 2016.

Safdar, et al. Clinical and economic consequences of ventilator-associated pneumonia: a systematic review. Crit Care Med. Oct. 2005;33(10):2184-93.

Tablan, et al. Guidelines for preventing health-care-associated pneumonia, 2003: recommendations of CDC and the Healthcare Infection Control Practices Advisory Committee. MMW R Recomm Rep.Mar. 26, 2004;53(RR-3):1-36.

Torres, et al. Pulmonary aspiration of gastric contents in patients receiving mechanical ventilation: the effect of body position. Ann Intern Med. Apr. 1, 1992;116(7):540-3.

\* cited by examiner

ACCELEROMETER AND WIRELESS NOTIFICATION SYSTEM

CROSS REFERENCE

This application claims the benefit of U.S. Provisional Patent Application No. 61/972,841, filed on Mar. 31, 2014, which is incorporated by reference in its entirety.

BACKGROUND OF THE INVENTION

Health conditions associated with posture can require careful management of patients' positions to reduce the risk of the health condition worsening. Adherence to recommended body angles can be challenging for patients to achieve and for caregivers to monitor on a frequent basis. Proper adherence can facilitate management of the health condition, increase patient compliance, and assist caregivers.

SUMMARY OF THE INVENTION

In some embodiments, the invention provides a method comprising: a) contacting a device to an upper body portion of a subject, wherein the device comprises an accelerometer, a gyroscope, and a processor, wherein the subject is at elevated risk of developing ventilator-associated pneumonia; b) detecting by the accelerometer a change in posture of the subject; c) detecting by the gyroscope the change in posture of the subject; and d) calculating by the processor an angle formed by a cross sectional plane of the device and a plane of reference based on the detected change in posture of the subject.

In some embodiments, the invention provides a device comprising: a) an attachment mechanism configured to attach the device to a subject who is at elevated risk of developing ventilator-associated pneumonia; b) an accelerometer configured to detect a change in posture of the subject; c) a gyroscope configured to detect the change in posture of the subject; and d) a processor configured to receive information from the accelerometer and the gyroscope, and determine an angle formed by a cross sectional plane of the device and a plane of reference based on the detected change in posture of the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
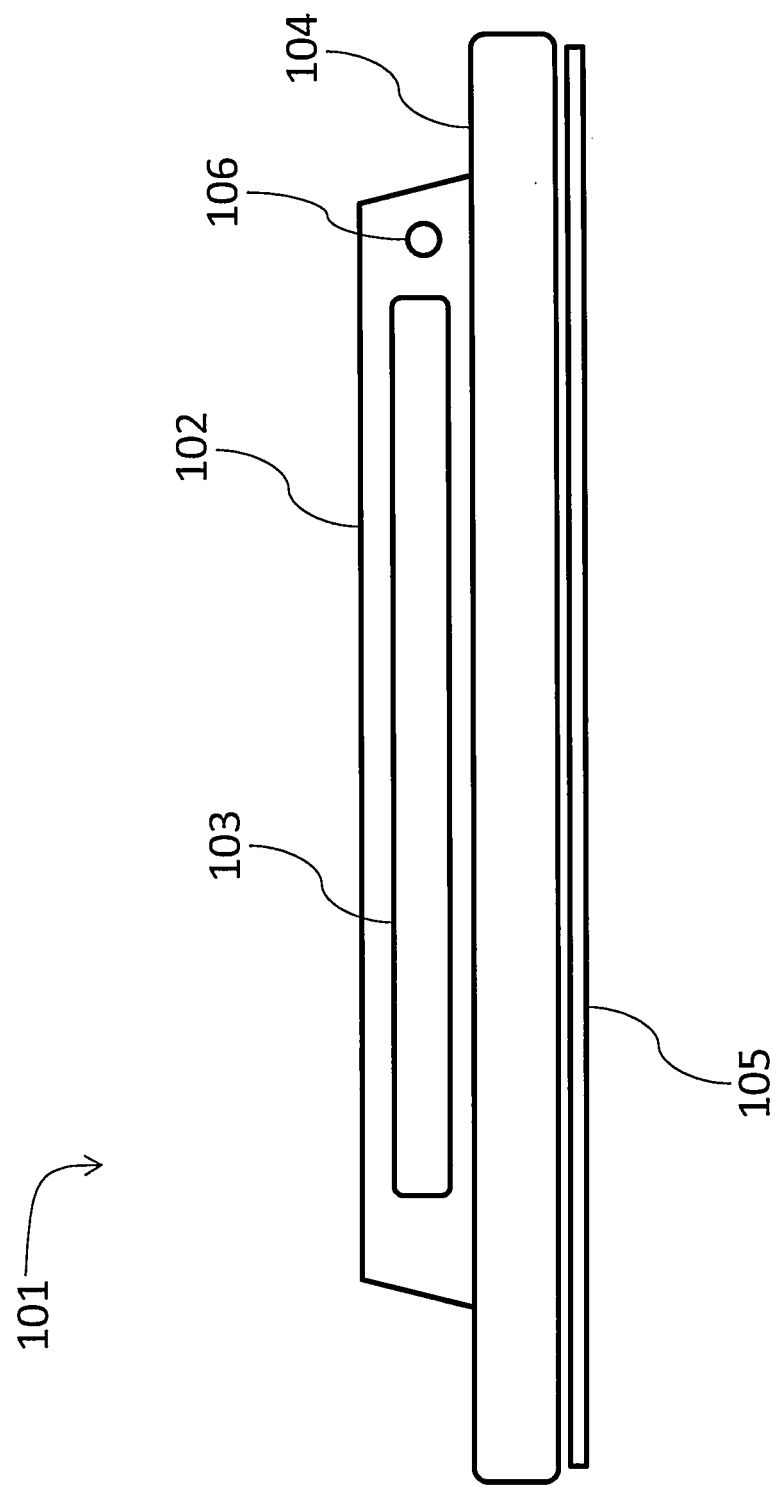
FIG. 1 is a schematic illustration of a device of the disclosure.

Nosocomial pneumonia, also known as hospital-acquired pneumonia, is a leading cause of mortality from hospital-acquired infections. Ventilator-associated pneumonia (VAP), a type of nosocomial pneumonia, can affect patients that have been intubated and placed on mechanical ventilation. Estimated to have an associated mortality rate of roughly 30%, ventilator-associated pneumonia can be a costly complication of patients on mechanical ventilators. Infections such as ventilator-associated pneumonia can place an added strain on intensive care units (ICUs) by increasing an ICU stay by an average of 4 days.

The pathogenesis of ventilator-associated pneumonia can include bacterial colonization of the stomach and oropharynx, followed by subsequent pulmonary aspiration of contaminated secretions that can lead to lung infection. Mechanically ventilated patients can be more susceptible to gastric bacterial infections as a result of widespread use of histamine receptor blockers and proton pump inhibitors, aimed to reduce gastrointestinal distress and ulceration in patients. Intubation can decrease competence of the lower esophageal sphincter, which in turn can increase the potential for aspiration, lung infection, and consequently ventilator-associated pneumonia. Symptoms of ventilator-associated pneumonia can include, for example, fever, chills, cough, thick mucus, green mucus, pus-like phlegm, blue color of nails, blue color of lips, nausea, vomiting, shortness of breath, low body temperature, purulent sputum, hypoxemia, and decreasing amounts of oxygen in the blood.

The angle of a patient's body in a hospital setting, for example, the angle between the patient's upper body and a plane of zero degree inclination, can influence the risk of aspiration and contaminated secretions traveling to the lungs, which can result in ventilator-associated pneumonia. When a patient's upper body is at an angle, for example, less than 30 degrees, the risk of a bacterial infection spreading to the lungs, and inducing pneumonia, can increase. Likewise, fluid can also move towards the lungs more easily when the patient's upper body is at an angle, for example, greater than 45 degrees. The risk of developing ventilator-associated pneumonia can be reduced by keeping the patient's body within a predetermined range, for example, from about 30 degrees to about 45 degrees.

A number of body positions can be recommended based on a person's needs and state of health. For example, a semi-recumbent position can represent a body positioned at an angle of about 30 to about 45 degrees, a recumbent position can indicate a reclined body position, and a supine position can indicate a body lying face-up on the back. Positioning a mechanically-ventilated patient in a semirecumbent position can be a low-cost prophylactic measure to decrease risk of ventilator-associated pneumonia. Intubated patients in the semi-recumbent position can have a lower incidence rate of ventilator-associated pneumonia compared with patients in the supine position. However, patient compliance with the optimal semi-recumbent position can be low due to many factors, for example, bedside caregivers can overestimate the angle of bed elevation; lack of communication between physicians and nurses; and convenience of obtaining vital signs in a completely recumbent position. Measurement of angles based on a device attached to, for example, a bed, can be inaccurate because the bed or the bed-floor can be uneven giving rise to an inherent error in the body angle calculation. A more implicit protocol detailing the desired body angle of intubated patients can assist caregivers. In clinical settings, patients, for example, bedridden patients, patients in an intensive care unit (ICU), intubated patients, and mechanically-ventilated patients can be at high risk of developing ventilator-associated pneumonia. Risk for ventilator-associated pneumonia can increase when the patient is allowed to rest in bed at a body angle of, for example, less than 30 degrees defined as the angle of the torso to a plane of zero degree inclination.

Management of neurological conditions and disorders, for example, idiopathic intracranial hypertension (IIH) and post-stroke care can include monitoring of a patient's posture. IIH can be characterized by, for example, increased cranial pressure in the absence of a tumor or other diseases. The cause of intracranial hypertension in IIH can be unknown. In some cases, IIH can be caused by or associated with, for example, an excess of cerebrospinal fluid (CSF), increased volume of blood or brain tissue, and obstruction of the veins that drain blood from the brain. Management of IIH can involve management of the angle of the patient's head and neck. Elevation of the head of the bed and keeping the head in a neutral position can minimize venous outflow resistance and promote displacement of CSF from the intracranial compartment to the spinal compartment. For example, elevation of the head to greater than 45 degrees can reduce intracranial pressure (ICP). Management of patients after a stroke can involve, for example, maintaining the subject's head at 0 degrees, or in some cases, at −15 degrees with respect to the body.

Pressure ulcers, also known as bedsores, can be managed by monitoring a patient's posture and adherence to recommended protocols that alleviate pressure and friction. Hospitalized patients, for example, bedridden patients, can be at an increased risk of developing hospital-acquired pressure ulcers (HAPUs) due to restricted movement, limited mobility, and decreased tissue circulation. During hospitalization, patients can be fitted with, for example, tubes, drains, and other health care equipment that can lead to pressure ulcers. Monitoring a patient's body positions and sending alerts to change positions when the patient has been in a position longer than a predetermined or recommended time can assist caregivers and patients, and reduce the risk of developing HAPUs.

Real-time monitoring of a patient's posture, for example, by measuring the patient's body angle, combined with an alerting system triggered by, for example, non-compliance by the patient, can result in increased patient compliance, decreased caregiver burden, decreased risk of posture-associated conditions, improved patient safety, reduced medical errors, and reduced hospital costs.
Device.

Disclosed herein is a device for monitoring posture of a subject. The device can be used used to manage a health condition associated with posture, for example, ventilator-associated pneumonia. In some embodiments, the device is used to reduce the risk of developing a health condition associated with posture. The device can assist caregivers in monitoring patient compliance of recommended postures by sending out alerts when the body angle is not within a predetermined range.

FIG. 1 is a schematic illustration of a non-limiting example of a device 101 of the disclosure. Device 101 comprises housing 102, angle measurement device 103, adhesive layers 104, and wireless transmitter 106. Housing 102 can be configured to shield angle measurement device 103 and wireless transmitter 106 from, for example, radiation from an X-Ray machine. Angle measurement device 103 can be configured to detect or approximate the body angle of a patient reclining in a hospital bed. The body angle can be, for example, an upper body angle measured as the vector of the torso, or the vector of a cross section of the device, with respect to a plane of zero degree inclination. Angle measurement device 103 can comprise an accelerometer and a battery configured to power both the angle measurement device and wireless transmitter 106. Adhesive layers 104 can be configured to adhere device 101 to a body surface 105 of a patient, such as skin or a garment. A device can have several layers of adhesive material. Each adhesive layer can be peeled off sequentially after each use, so that device 101 can be reapplied to patient body surface 105 as needed. Wireless transmitter 106 can be configured to transmit data generated by angle measurement device 103 to a monitoring station. Wireless transmitter 106 can comprise an RF transmitter or other wireless transmitting system. Data transmitted by the device can be monitored wirelessly. The data can be interpreted by a remote computing terminal. If a body angle measured by the angle measurement system is outside a selected range, then an alarm can alert the patient or a caregiver of the improper patient body angle.

Figure 2:
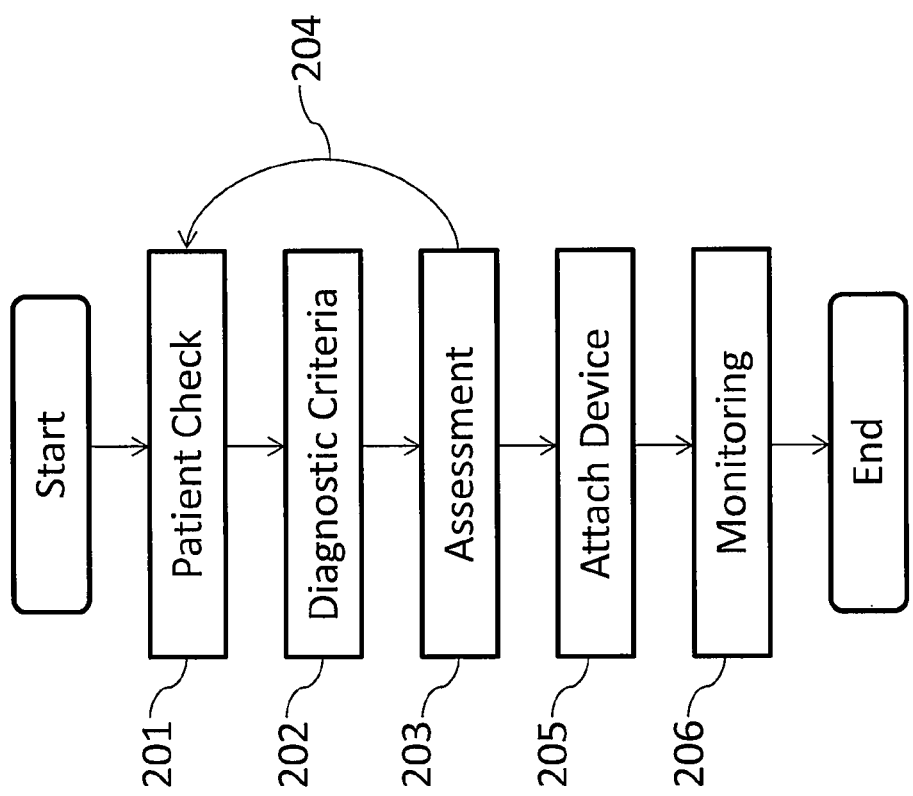
FIG. 2 illustrates a method for using a device of the disclosure for monitoring a subject.

FIG. 2 is a flowchart describing non-limiting, illustrative clinical criteria for a caregiver to determine use of device 101. When a patient is placed on bed rest, a caregiver can check 201 the patient and evaluate the patient based on certain diagnostic criteria 202, for example, breathing problems, risk of aspiration, and bacterial infection. Based on the check 201, the caregiver can assess 203 the patient for risk of ventilator-associated pneumonia. If the assessment is negative 204, the caregiver can check 201 the patient again at a later date. If the assessment 203 is positive, the caregiver can recommend attaching device 101. The caregiver can attach 205 the device to a body surface of the patient to measure a body angle of the patient. The body angle can be monitored wirelessly 206.

Figure 3:
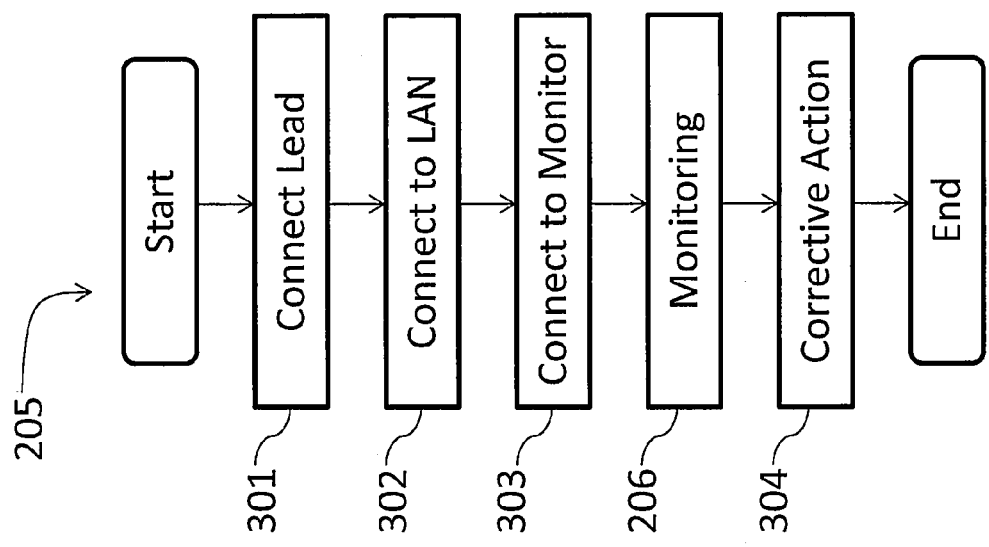
FIG. 3 illustrates the operational methods for using a device of the disclosure.

FIG. 3 is a flowchart describing non-limiting, illustrative operational criteria of device 101. The device is attached 205 to patient body surface 105 using adhesive layer 104. The caregiver can wirelessly connect 302 device 101 to a local area network (LAN), which can be subsequently connected to a monitoring terminal 303. The device can be monitored 206 remotely by a caregiver or by an automated system. If the monitoring system detects an angle outside a predetermined range, an audio or visual alarm can be activated and the caregiver can take corrective action 304 to return the patient body angle to a level within the desired range.

Figure 4:
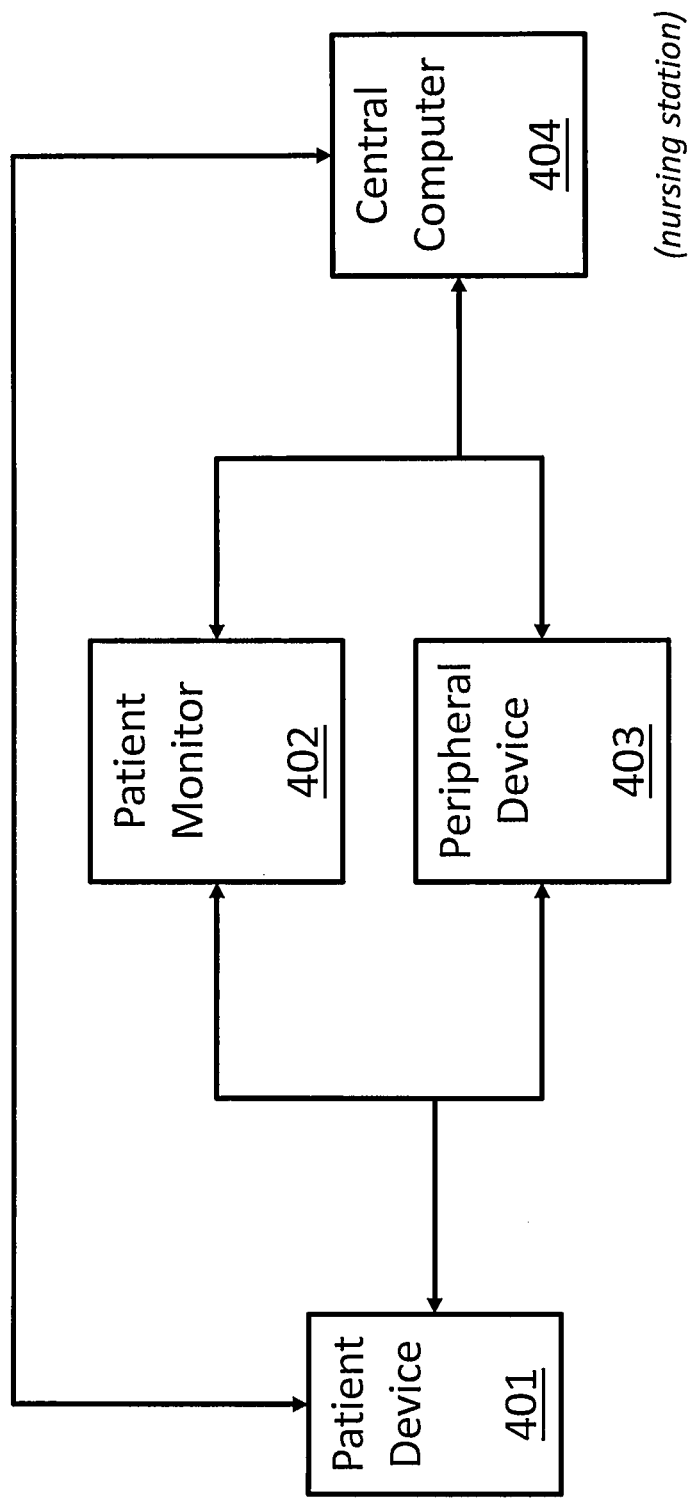
FIG. 4 schematically illustrates the integration of a device of the disclosure into a wireless system for monitoring patient metrics.

FIG. 4 is a flowchart describing a non-limiting example of the integration of device 101 into a wireless system for monitoring patient metrics. Patient device 401 can be configured to communicate with a central computer 404, which can be located at a central monitoring location or nursing station. Patient device 401 can be further configured to communicate with patient monitor 402, which can be located near or integrated into the patient bed. Patient monitor 402 can be further configured to communicate with central computer 404. Patient device 401 can further be configured to communicate with peripheral device 403, which can comprise a personal computer, tablet or smartphone. Peripheral device 403 can be further configured to communicate with patient monitor 402 or central computer 404.

Figure 5:
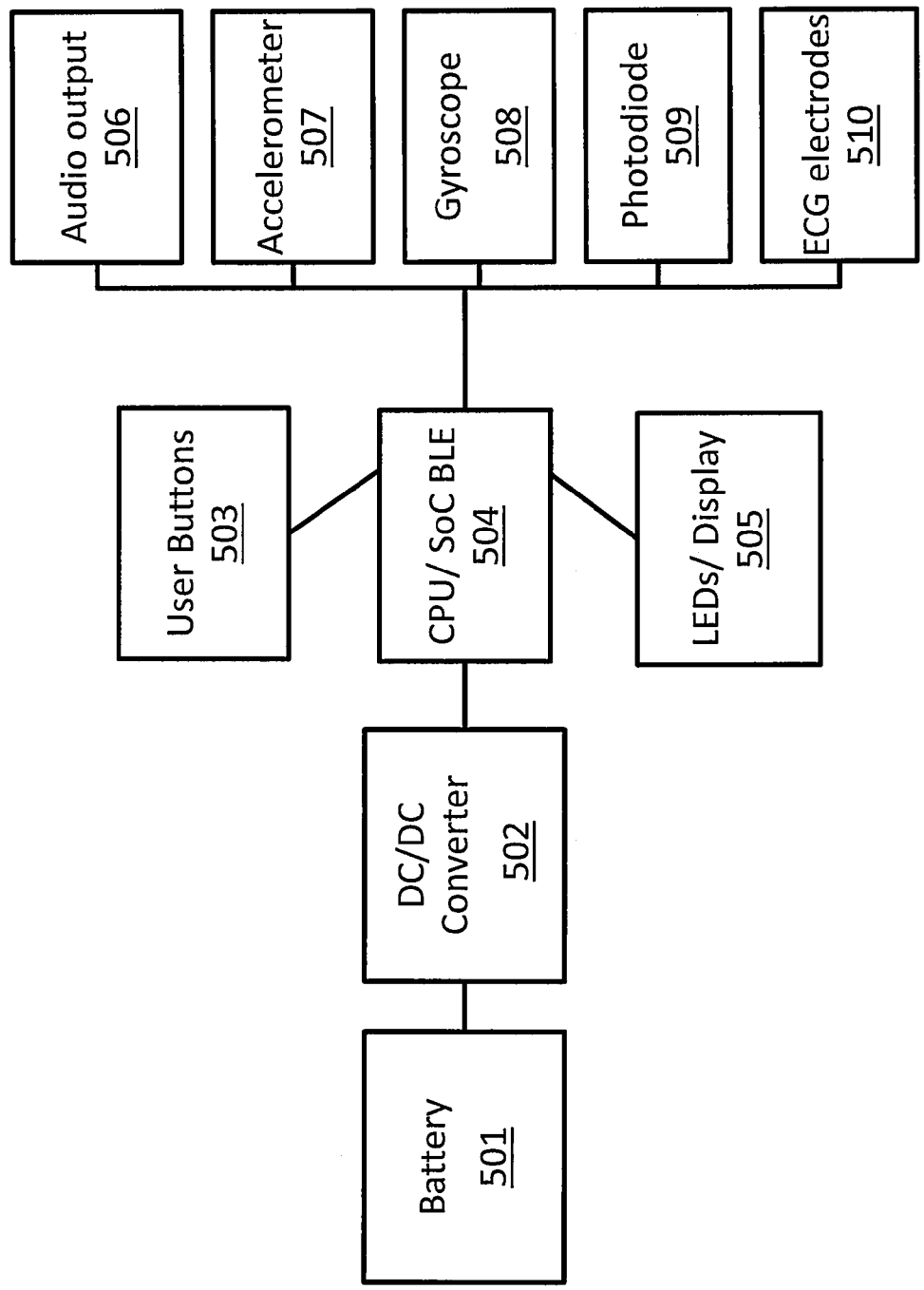
FIG. 5 schematically illustrates a system map showing the functional interrelationship of elements in a device of the disclosure.

FIG. 5 is a system map describing a non-limiting example of the functional interrelationship of elements in device 101. Battery 501 is operatively connected to DC/DC converter 502. DC/DC converter 502 is configured to convert the voltage produced by battery 501 to a level usable by other elements of device 101. DC/DC converter 502 is operatively connected to CPU/SoC Bluetooth low energy (BLE) 504, which is configured to manage further elements of device 101 and to communicate wirelessly with other devices. User buttons 503 are configured to confer caregiver instructions to CPU/SoC BLE 504. The instructions can include, for example, the optimal patient orientation angle. LEDs/Display 505 and audio output 506 can be configured to indicate visually or audibly, respectively, the status of the patient's orientation or body angle. Accelerometer 507 and gyroscope 508 can be configured to collect measurements corresponding to changes in patient body angle or orientation and transmit the information to CPU/SoC BLE 504. Photodiode 509 can be configured to interrogate patient surface blood vessels optically to determine patient blood oxygenation. ECG electrodes 510 can be configured to be placed in a manner configured to measure the electrical activity of a patient's heart.

Figure 6:
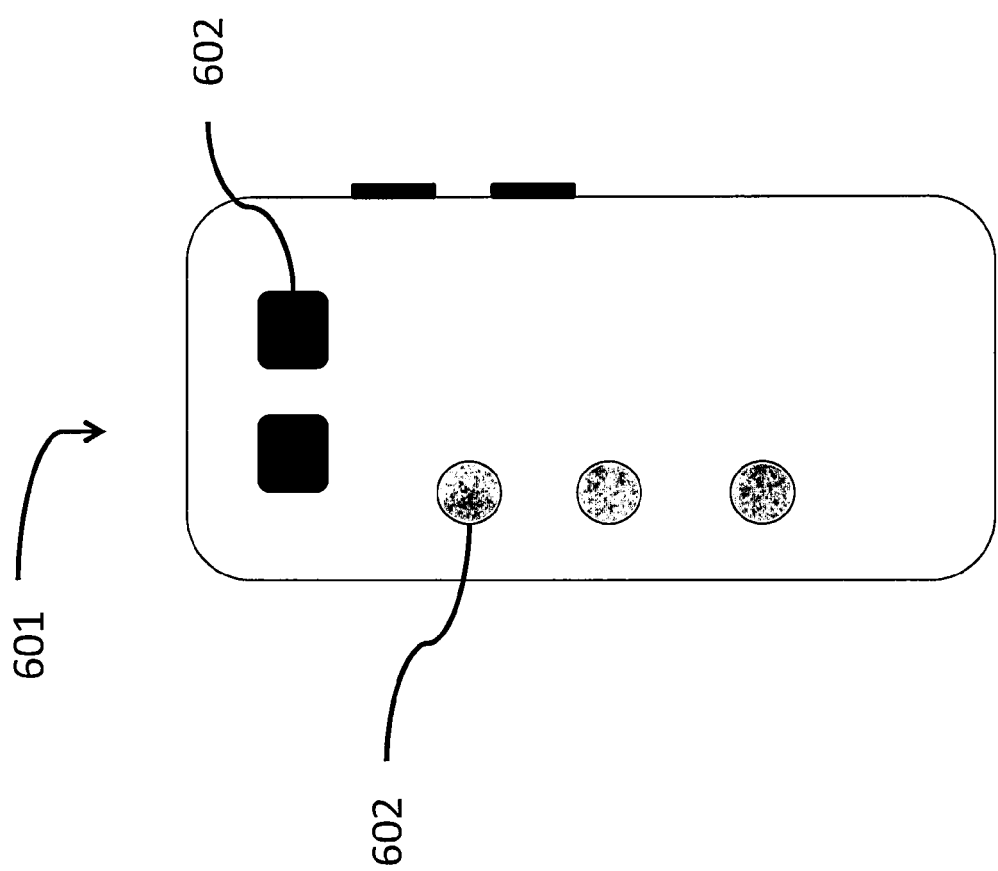
FIG. 6 schematically illustrates a caregiver-facing surface of a device of the disclosure.

FIG. 6 is a non-limiting example of a caregiver-facing surface 601 of device 101. Interface buttons 602 can be configured to receive instructions from a caregiver. LEDs 602 can be configured to indicate certain patient metrics to a caregiver in a succinct fashion.

A device described herein can comprise an accelerometer. The accelerometer can be single or multi-axis, for example, one-axis, two-axis, or three-axis, and can be used to detect patient orientation in one or more axes. In some embodiments, the accelerometer is a 3-axis accelerometer. In some embodiments, the accelerometer is a small micro electro-mechanical systems (MEMS)-based system. The accelerometer can have analog or digital outputs. In some embodiments, the device comprises one accelerometer. The device can incorporate multiple accelerometers, for example, 1, 2, 3, 4, 5, 6, 7, 8, 9, or 10 accelerometers.

A device described herein can comprise a gyroscope. The device can employ, for example, 1, 2, 3, 4, 5, 6, 7, 8, 9, or 10 gyroscopes. The gyroscope can be single or multi-axis, for example, one-axis, two-axis, or three-axis. In some embodiments, the device uses one gyroscope. In some embodiments, the device uses 2 gyroscopes. In some embodiments, the gyroscope is a small micro electro-mechanical systems (MEMS)-based system. Measurements from an accelerometer and a gyroscope can be combined to produce more accurate estimate of position, for example, a subject's position, posture, or body angle. The measurements can be combined in a weighted fashion. An initial or reference position can be specified for the measurement.

A device described herein can ascertain the three-dimensional orientation of a patient's body with respect to gravity. For example, the device for monitoring patient metrics can use three-dimensional vector information to derive patient thorax elevation via the vector dot product. The device can operate in an ultra-low power, low-resolution state to detect motion or a change in patient orientation. The device can shift to a higher-power, higher-resolution mode that is only active immediately after motion or a change in orientation is detected. The higher-power, higher-resolution mode can be used to characterize motion or obtain more precise orientation information.

A device described herein can include sensors for measuring vital signs of the subject, for example, heart rate, breathing rate, blood pressure, and temperature. The device can include sensors for humidity. The device can include, for example, LEDs and a photodiode, on a face of the device in contact with a subject's skin to permit measurement of blood oxygenation. The device can include sensors for monitoring motion of the chest wall.

A device described herein can be attached using any attachment mechanism. Non-limiting examples of attachment mechanisms include adhesive; patches; medical grade adhesive patches such as silicone, acrylic, and foam; straps; clips; hooks; velcro; clasps; mechanical attachments; belt; tape; glue; and magnets. The device can be a pendant, button, or ECG lead-type attachment to a body surface of the patient.

A device described herein can be attached to any suitable body surface of the subject. The device can be attached to a subject's skin. The device can be unattached from the subject's body. The device can be attached to or placed in proximity of an upper body portion of the subject, for example, chest, thorax, sternum, clavicle, back, trunk, torso, or abdomen. The device can be attached or placed in proximity of the subject's head, neck, cervical spine, hips, tailbone, buttocks, shoulder, shoulder blades, spine, arms, legs, heels, ankles, ears, lower back, or knees. In some embodiments, the device is attached to a subject's chest. In some embodiments, the device is attached to a sternal surface of the subject. In some embodiments, the device is attached below the subject's clavicle. In some embodiments, the device is attached to a suitable body part affected by a pressure ulcer.

A device can be attached to or placed in proximity of a subject. The device can be attached to a subject's garment or clothing, for example, hospital gown, smock, shirt, jacket, or a sweater. The device can be attached to, for example, head of bed, headboard, bed, chair, sofa, or other furniture in proximity to the subject. The device can be attached to, for example, a mattress, a pillow, a comforter, or a sofa.

In some embodiments, a device is more efficient at making measurements and monitoring a subject when attached to the subject compared to when the device is attached in proximity of the subject, for example, a bed. The device can detect movements of the subjects with greater accuracy, speed, and lower false alert rate when attached to a subject than in proximity to the subject, such as attached to a bed. A body angle measured using a device attached to, for example, a bed, can be inaccurate or difficult to measure. The bed or the bed floor can be uneven, tilted, or at a degree of inclination greater than zero from gravity, which can result in inaccurate measurements of body angle from the device attached to the bed. A device attached to a subject that measures an angle relative to a true zero degree inclination from gravity can be more accurate at measuring body angles.

A device can be attached in any suitable orientation, position or alignment. For example, the device can be attached in a vertical position or a horizontal position. In some embodiments, the device is attached in vertical alignment with the subject's sternum. In some embodiments, the device is attached in horizontal alignment with the clavicle.

A device of the invention can have a design to cause minimal discomfort to a subject. The device can have a design to cause minimal or no interference in any activity of the subject, for example, breathing, sleeping, eating, drinking, or talking. The device can be used with any subject equally well irrespective of age, sex, weight, size, body shape, or any physical condition. For example, the subject can be male, female, child, infant, old, young, obese, thin, emaciated, tall, or short. The device can have a minimal attachment surface or footprint on a subject, for example, about 0.5 inches by about 0.5 inches, about 0.5 inches by about 1 inches, about 0.5 inches by about 2 inches, about 0.5 inches by about 3 inches, about 0.5 inches by about 4 inches, about 1 inch by about 1 inch, about 1 inch by about 2 inches, about 1 inch by about 3 inches, about 1 inch by about 4 inches, about 2 inches by about 2 inches, about 2 inches by about 3 inches, about 2 inches by about 4 inches, about 2 inches by about 5 inches, about 3 inches by about 3 inches, about 4 inches by about 3 inches, about 5 inches by about 3 inches, about 6 inches by about 3 inches, or about 7 inches by about 3 inches, about 5 inches by about 4 inches, about 6 inches by about 4 inches, about 7 inches by about 4 inches, about 5 inches by about 5 inches, about 6 inches by about 5 inches, about 7 inches by about 5 inches, about 6 inches by about 6 inches, or about 7 inches by about 6 inches.

The device can be modified to conform to hospital or healthcare best practices. The device can comprise any form factor that is adapted specifically to a purpose.

A device described herein can generate an alert when a measurement made by the device is outside a predetermined range for a period of time. In some embodiments, the predetermined range for monitoring upper body posture can be from about 30 degrees to about 45 degrees.

A device can be configured to monitor any suitable range of measurements in any suitable increment. Non-limiting examples of range of angles that can be measured by the device include about 0 degrees to about 5 degrees, about 5 degrees to about 10 degrees, about 10 degrees to about 15 degrees, about 15 degrees to about 20 degrees, about 20 degrees to about 25 degrees, about 25 degrees to about 30 degrees, about 30 degrees to about 35 degrees, about 35 degrees to about 40 degrees, about 40 degrees to about 45 degrees, about 45 degrees to about 50 degrees, about 50 degrees to about 55 degrees, about 55 degrees to about 60 degrees, about 60 degrees to about 65 degrees, about 65 degrees to about 70 degrees, about 70 degrees to about 75 degrees, about 75 degrees to about 80 degrees, about 80 degrees to about 85 degrees, about 85 degrees to about 90 degrees, about 0 degrees to about −5 degrees, about −5 degrees to about −10 degrees, about −10 degrees to about −15 degrees, about −15 degrees to about −20 degrees, about −20 degrees to about −25 degrees, about −25 degrees to about −30 degrees, about −30 degrees to about −35 degrees, about −35 degrees to about −40 degrees, about −40 degrees to about −45 degrees, about −45 degrees to about −50 degrees, about −50 degrees to about −55 degrees, about −55 degrees to about −60 degrees, about −60 degrees to about −65 degrees, about −65 degrees to about −70 degrees, about −70 degrees to about −75 degrees, about −75 degrees to about −80 degrees, about −80 degrees to about −85 degrees, and about −85 degrees to about −90 degrees.

An amount of time for which a subject is outside a predetermined range before an alert is generated by the device can be user-defined and can be, for example, about 1 second, about 2 seconds, about 3 seconds, about 4 seconds, about 5 seconds, about 10 seconds, about 15 seconds, about 30 seconds, about 45 seconds, about 1 minute, about 5 minutes, about 10 minutes, about 30 minutes, or 60 minutes. For example, the device can be configured to generate an alert only when the subject is outside a predetermined range of upper body angles for more than 5 seconds.

An alert generated by a device described herein can be, for example, auditory, visual, electronic, textual, or a combination thereof. The alerts can be based on, for example, severity of a subject's posture, time period of non-compliance of subject, emergency, a subject's discomfort, or a combination thereof. The alert generated by the device can be transmitted to a caregiver by any suitable mode of transmission.

The alert generated on a device can be paused or snoozed for a predetermined interval of time, while the device continues to acquire data. The snooze time can be, for example, 1 second, 2 seconds, 5 seconds, 10 seconds, 15 seconds, 30 seconds, 45 seconds, 1 minute, 5 minutes, 10 minutes, 30 minutes, or 1 hour.

A device can comprise a computer system that can receive data associated with, for example, detected angles, posture, and movement. The data received by the computer system can then be compared by a processor of the computer system to a reference to determine whether the subject has improper posture. Non-limiting examples of references that can be used by the computer system include past measurements from the subject, measurements from a healthy subject, statistical averages of the data being measured, and reference texts. The computer system can then output a result of the determination.

A device described herein can comprise a processor coupled to a transmitter configured to transmit data, including alerts, from the device to another location, for example, nursing station, caregiver, hospital, clinic, or a doctor's office. The transmitter can be configured to transmit data wirelessly, for example, via Bluetooth, wireless networks, cell phone networks, a cloud network, or the internet. For example, the device can use Bluetooth to connect to an analysis device, such as, a cell phone or computer system. The transmission can be wired. The processor can be configured to transmit data to a plurality of receivers in a plurality of geographic locations. In some embodiments, the processor can transmit data over a distance of about 1 mile, about 2 miles, about 3 miles, about 4 miles, about 5 miles, about 6 miles, about 7 miles, about 8 miles, about 9 miles, about 10 miles, or over about 50 miles. The device can comprise a Global Positioning System (GPS).

The reliability or likelihood of a device described herein to generate an alert corresponding to a subject being outside a predetermined measurement range can be, for example, at least or no greater than about 100%, at least or no greater than about 99%, at least or no greater than about 98%, at least or no greater than about 97%, at least or no greater than about 96%, at least or no greater than about 95%, at least or no greater than about 94%, at least or no greater than about 93%, at least or no greater than about 92%, at least or no greater than about 91%, at least or no greater than about 90%, at least or no greater than about 85%, at least or no greater than about 80%, or at least or no greater than about 75%. The likelihood of the device generating a false alert, which can be an alert when the subject is not outside a predetermined range, can be, for example, at least or no greater than about 0.1%, at least or no greater than about 0.2%, at least or no greater than about 0.3%, at least or no greater than about 0.4%, at least or no greater than about 0.5%, at least or no greater than about 0.6%, at least or no greater than about 0.7%, at least or no greater than about 0.8%, at least or no greater than about 0.9%, at least or no greater than about 1%, at least or no greater than about 2%, at least or no greater than about 3%, at least or no greater than about 4%, at least or no greater than about 5%, at least or no greater than about 6%, at least or no greater than about 7%, at least or no greater than about 8%, at least or no greater than about 9%, or at least or no greater than about 10%.

A device of the invention can have a measurement range of, for example, about ±90 degrees/sec, about ±250 degrees/sec, about ±500 degrees/sec, about ±1000 degrees/sec, or about ±2000 degrees/sec. The device can have a measurement range of, for example, about ±0.1 g-force, about ±0.2 g-force, about ±0.3 g-force, about ±0.4 g-force, about ±0.5 g-force, about ±0.6 g-force, about ±0.7 g-force, about ±0.8 g-force, about ±0.9 g-force, about ±1 g-force, about ±1.5 g-force, about ±2 g-force, about ±2.5 g-force, about ±3 g-force, about ±3.5 g-force, about ±4 g-force, about ±4.5 g-force, about ±5 g-force, about ±5.5 g-force, about ±6 g-force, about ±6.5 g-force, about ±7 g-force, about ±7.5 g-force, about ±8 g-force, about ±8.5 g-force, about ±9 g-force, about ±9.5 g-force, or about ±10 g-force.

A device described herein can make measurements continuously or at any suitable time interval. The time intervals can be defined by a user of the device. The measurements can be made at intervals of, for example, about 0.1 seconds, about 0.2 seconds, about 0.3 seconds, about 0.4 seconds, about 0.5 seconds, about 0.6 seconds, about 0.7 seconds, about 0.8 seconds, about 0.9 seconds, about 1 second, about 2 seconds, about 3 seconds, about 4 seconds, about 5 seconds, about 10 seconds, about 15 seconds, about 30 seconds, about 45 seconds, about 1 minute, about 5 minutes, about 10 minutes, about 30 minutes, or about 60 minutes.

A device described herein can have a measurement accuracy, or a margin of error of, for example, about 0.01 degrees, about 0.02 degrees, about 0.03 degrees, about 0.04 degrees, about 0.05 degrees, about 0.06 degrees, about 0.07 degrees, about 0.08 degrees, about 0.09 degrees, about 0.1 degrees, about 0.2 degrees, about 0.3 degrees, about 0.4 degrees, about 0.5 degrees, about 0.6 degrees, about 0.7 degrees, about 0.8 degrees, about 0.9 degrees, about 1 degree, about 1.5 degrees, about 2 degrees, about 2.5 degrees, about 3 degrees, about 3.5 degrees, about 4 degrees, about 4.5 degrees, about 5 degrees, or about 5.5 degrees.

A device described herein can have a sensitivity of, for example, about 0.01 degrees, about 0.02 degrees, about 0.03 degrees, about 0.04 degrees, about 0.05 degrees, about 0.06 degrees, about 0.07 degrees, about 0.08 degrees, about 0.09 degrees, about 0.1 degrees, about 0.2 degrees, about 0.3 degrees, about 0.4 degrees, about 0.5 degrees, about 0.6 degrees, about 0.7 degrees, about 0.8 degrees, about 0.9 degrees, or about 1 degree.

The operating temperature of a device of the invention can be from about −40° C. to about +85° C. In some embodiments, the device is operated at ambient temperature.

Non-limiting examples of device shape include a cube, a sphere, a cylinder, a square prism, a rectangular prism, a rounded rectangular prism, and a disk. A device described herein can have a height (H), width (W), and depth (D), each independently of about 0.01 inches, about 0.02 inches, about 0.03 inches, about 0.04 inches, about 0.05 inches, about 0.1 inches, about 0.15 inches, about 0.2 inches, about 0.21 inches, about 0.22 inches, about 0.23 inches, about 0.24 inches, about 0.25 inches, about 0.26 inches, about 0.27 inches, about 0.28 inches, about 0.29 inches, about 0.3 inches, about 0.35 inches, about 0.4 inches, about 0.45 inches, about 0.5 inches, about 0.6 inches, about 0.7 inches, about 0.8 inches, about 0.9 inches, about 1 inch, about 1.1 inches, about 1.2 inches, about 1.3 inches, about 1.4 inches, about 1.5 inches, about 1.6 inches, about 1.7 inches, about 1.8 inches, about 1.9 inches, about 2 inches, about 2.5 inches, about 3 inches, about 3.5 inches, about 4 inches, about 4.5 inches, or about 5 inches. In some embodiments, the device is a cube. In some embodiments, the device is a rounded rectangular prism. In some embodiments, the device can have dimensions of about 2 inches H×about 1 inch W×about 0.5 inches D. In some embodiments, the device can have dimensions of about 1 inch H×about 1 inch W×about 0.25 inches D.

A device of the invention can have a total mass of, for example, about 1 gram, about 2 grams, about 3 grams, about 4 grams, about 5 grams, about 6 grams, about 7 grams, about 8 grams, about 9 grams, about 10 grams, about 15 grams, about 20 grams, about 25 grams, about 30 grams, about 35 grams, about 40 grams, about 45 grams, about 50 grams, about 60 grams, about 70 grams, about 80 grams, about 90 grams, about 100 grams, about 110 grams, about 120 grams, about 130 grams, about 140 grams, about 150 grams, about 200 grams, about 250 grams, about 300 grams, about 350 grams, about 400 grams, about 450 grams, about 500 grams, about 550 grams, about 600 grams, about 650 grams, about 700 grams, about 750 grams, about 800 grams, about 850 grams, about 900 grams, about 950 grams, or about 1000 grams. In some embodiments, the total mass of the device can be from about 100 grams to about 300 grams.

Any tool, interface, engine, application, program, service, command, or other executable item can be provided as a module encoded on a computer-readable medium in computer executable code. In some embodiments, the invention provides a computer-readable medium encoded therein computer-executable code that encodes a method for performing any action described herein, wherein the method comprises providing a system comprising any number of modules described herein, each module performing any function described herein to provide a result, such as an output, to a user.

Applications of a Device of the Invention.

A device described herein can be used to manage a subject with a health condition associated with posture. The device can be used to manage a subject at risk of developing a health condition associated with posture. The device can be used to reduce the risk of developing a health condition associated with posture. Non-limiting examples of health conditions include ventilator-associated pneumonia, idiopathic intracranial hypertension, neurological disorders, stroke, post-stroke care, pressure ulcers, hospital-acquired pressure ulcers, bedsores, asthma, allergy, bronchitis, chronic obstructive pulmonary disease, respiratory disorder, pneumonia, nosocomial pneumonia, acute lung injury, apnea, respiratory arrest, respiratory acidosis, Guillain-Barré syndrome, myasthenia gravis, spinal cord injury, respiratory distress, tachypnea, hypoxemia, hypotension, sepsis, shock, congestive heart failure, neurological disease such as muscular dystrophy, amyotrophic sclerosis, sudden infant death syndrome, dizziness, back problems, chemical pneumonitis, aspiration pneumonia, dysphagia, superior mesenteric artery syndrome, breathing disorders, respiratory disorders, pregnancy, surgery, and conditions associated with pulmonary aspiration such as nasogastric intubation. Monitoring posture of a subject with nasogastric tube can reduce the risk of aspiration. In some embodiments, the health condition is ventilator-associated pneumonia. In some embodiments, the condition is intracranial hypertension. In some embodiments, the device is used for post-stroke care.

In some embodiments, the condition is hospital-acquired pressure ulcer. In some embodiments, the subject is bedridden.

A device of the invention can be used to reduce the risk of acquiring a health condition described herein. The risk can be reduced by, for example, about 10%, about 20%, about 30%, about 40%, about 50%, about 60%, about 70%, about 80%, about 90%, or about 100%.

In some embodiments, a device of the invention is used to reduce the risk of ventilator-associated pneumonia in mechanically-ventilated subjects. The risk of ventilator-associated pneumonia can be reduced by, for example, about 10%, about 20%, about 30%, about 40%, about 50%, about 60%, about 70%, about 80%, about 90%, or about 100%.

A device described herein can be used to monitor a subject's posture in any environment or care setting. Non-limiting examples of care settings include clinic, hospital, doctor's office, home, school, nursing home, intensive care unit, emergency department, community care center, old age home, and ambulance.

A subject can be, for example, an elderly adult, an adult, an adolescent, a child, a toddler, or an infant. A subject can be a patient. A subject can be bedridden. A subject can be intubated. A subject can be on mechanical ventilation.

A user of a device can be a subject. A user can be a caregiver, for example, a family member of the subject, legal guardian of the subject, or a healthcare professional. Non-limiting examples of healthcare professionals include physicians, nurses, respiratory therapists, paramedics, pulmonologists, pulmonary specialists, physician assistants, medical technicians, surgeons, surgeon's assistants, surgical technologists, chiropractors, clinical officers, physical therapists, occupational therapists, emergency medical technicians, clinicians, and radiographers.

The method can include escalating alerts at a central monitoring station. For example, the device can incorporate an indicator in the form of escalating visual alerts at a central nursing station in the form of a color coded indication of patient's status. A visual indicator can be in the form of a graph depicting patient status, for example, posture or movement, against time. The system can incorporate audio alerts relating to abnormal or dangerous patient metrics. In some embodiments, a system for monitoring patient metrics includes various visual or audio status indicators on a device in contact with a patient.

A device can be used to maintain and monitor a subject's posture at any suitable body angle recommended for a health condition. The angle can be measured between a cross sectional plane of the device attached to or in proximity of a body part, for which the angle is being measured, and a plane of zero degree inclination. Non-limiting examples of body angles that can be measured and monitored by the device include about −5 degrees, about −10 degrees, about −15 degrees, about −20 degrees, about −25 degrees, about −30 degrees, about −35 degrees, about −40 degrees, about −45 degrees, about −50 degrees, about −55 degrees, about −60 degrees, about −65 degrees, about −70 degrees, about −75 degrees, about −80 degrees, about −85 degrees, about −90 degrees, about 0 degrees, about 5 degrees, about 10 degrees, about 15 degrees, about 20 degrees, about 25 degrees, about 26 degrees, about 27 degrees, about 28 degrees, about 29 degrees, about 30 degrees, about 31 degrees, about 32 degrees, about 33 degrees, about 34 degrees, about 35 degrees, about 36 degrees, about 37 degrees, about 38 degrees, about 39 degrees, about 40 degrees, about 41 degrees, about 42 degrees, about 43 degrees, about 44 degrees, about 45 degrees, about 46 degrees, about 47 degrees, about 48 degrees, about 49 degrees, about 50 degrees, about 55 degrees, about 60 degrees, about 65 degrees, about 70 degrees, about 75 degrees, about 80 degrees, about 85 degrees, and about 90 degrees.

A device can detect sliding of the patient from a hospital bed, for example, the device can detect sliding of the patient toward the head or foot of the hospital bed, or other rapid motions that cause a sudden change in posture or angle.

EXAMPLES

Example 1

Use of a Device of the Invention for Managing Posture of a Subject Receiving mechanical ventilation An elderly patient with respiratory distress is admitted to an intensive care unit of a hospital. The patient is intubated and placed on mechanical ventilation. To lower the risk of the patient developing ventilator-associated pneumonia, a device of the invention is affixed to the patient's sternal region to monitor upper body movements and posture.

A nurse turns on a computer system, for example, a tablet, adjacent to a vital sign monitor of the patient and opens an application of the device. In the application, the nurse enters data related to the patient, including new or old patient, patient name, patient medical record number (MRN), and name of provider, such as nurse or doctor. An initial setup screen of the application on the computer system guides the setup of the device. The first step in the setup screen is activation of the device. The nurse unpackages a device from product packaging and holds the "ON/OFF" button for about 5 seconds until the setup screen displays "Connection Established", indicating that a connection between the device and the computer system has been established. Information about the patient is then transmitted from the computer system to the device. The setup screen displays "Device linked to patient" and patient information after the device is associated with the patient and provider identifiers.

The nurse cleans the skin around the chest area of the patient with a sterile antiseptic wipe in circular expanding pattern. Covering around the adhesive surface of the device is removed. Using the adhesive surface, the nurse attaches the device on the patient's sternal surface in vertical alignment with the patient's sternum. Moderate pressure is applied to ensure secure attachment of the device to the patient.

After setup is complete, the display on the device begins to show real-time angle measurement of the patient's upper body. The device has an "Adjust Range" tab that is tapped to adjust the range of the upper body angle by selecting appropriate values for minimum and maximum angles, and tapping "Confirm". In this example, the maximum angle is set at 45 degrees and the minimum angle is set at 30 degrees.

The device displays the real-time angle at all times. The measurement is displayed in green text when the detected angle is within the defined range of about 30 degrees to about 45 degrees. In case of slight misalignment of the patient's body, for example, when the patient's upper body angle is 26 degrees, the device displays the measurement in yellow text. In case of severe misalignment of the patient's posture, for example, the patient's upper body angle is 71 degrees for more than 30 seconds, the measurement is displayed as red text. When the patient continues to be severely misaligned, for example, a 71 degree angle for more than 5 minutes, the red text starts blinking, thus providing a flashing red visual cue to notify the nurse or other providers that the patient's posture needs adjustment immediately. The device can be snoozed at any time by tapping the "Snooze" button, which pauses the display, while measurements continue to be acquired and stored. To return to the normal display, the user can tap "Wake Up". When the patient is returned to the proper position, the measurement returns to green color. If the reading does not change immediately, the "Measure Now" button can be tapped.

In the event of an error, for example, the device loses connectivity or the battery dies, an appropriate notification is displayed and a troubleshooting guide is available. A "Coordinator View" button permits authorized users to perform additional functions, for example, advanced configuration such as "Test Connectivity" and "Set Sampling Rate", troubleshooting, and view and export data.

The device can be removed from the patient during bathing, application of skin treatments, or other procedures such as chest X-ray. The device can be turned off by clicking "Button A" twice. After removal of the device, the patient's skin is cleaned with sterile antiseptic wipe, using wide margins and in circular expanding pattern. The device is also cleaned with a sterile antiseptic wipe. Depending on the adhesive stability, the same adhesive layer can be used for reattaching to patient or a new adhesive layer can be used after removing the used adhesive layer.

When the patient is discharged, or develops a contraindication that no longer requires posture monitoring, the device is removed from the patient, cleaned with a sterile antiseptic wipe, placed in a plastic bag provided at the central nursing station, and returned to a designated bin.

Example 2

Pilot Study to Determine Efficacy of the Disclosed Device for Reducing Ventilator-Associated Pneumonia Purpose: The purpose of the study is to evaluate the efficacy of a device of the invention in managing mechanically-ventilated patients and reducing the risk of developing ventilator-associated pneumonia.

Methods: In a hospital, 100 mechanically-ventilated subjects enter a placebo-controlled, double-blind, randomized study.

1) Experimental arm: 50 mechanically-ventilated subjects are configured with a device as outlined in Example 1.
2) Control arm: 50 mechanically-ventilated subjects are configured with a placebo device not equipped to monitor posture metrics.

Subjects in the experimental and control arms are inspected at regular time intervals post-attachment, for example, Day 0, Day 1, Day 2, Day 3, and Day 7, for symptoms of ventilator-associated pneumonia. Since ventilator-associated pneumonia can develop, for example, about 48 to about 72 hours post endotracheal intubation, Day 0 can correspond to the start day of mechanical ventilation. Student's t test is used to assess the significance of the device in reducing the risk of developing ventilator-associated pneumonia in the experimental arm compared with the control arm.

Subjects in the experimental group are monitored at regular time intervals post-attachment, for example, every 15 minutes, every 30 minutes, or every 60 minutes. Parameters monitored at each time interval include, for example, upper body angle as measured by visual inspection and that measured by the device. The angles measured by the device and visual inspection are compared to determine the margin of error in the device-measured angles. Based on the data, sensitivity of the device is calculated.

Subjects in the experimental group are monitored at regular time intervals post-attachment, for example, every 30 minutes for 24 hours, for improper body angle by visual inspection and generation of an alert by the device. Each time an alert is generated, the patient is visually inspected to determine whether the patient's body angle is outside the predetermined range as detected by the device. The rate of false alert is determined by analyzing data related to the number of times an alert is generated when the body angle is within the predetermined range as measured by visual inspection. The reliability of alert generation by the device is also calculated by analyzing data related to the number of times the patient is outside the predetermined range and whether an alert is generated by the device.

Example 3

Computer Architectures

Figure 7:
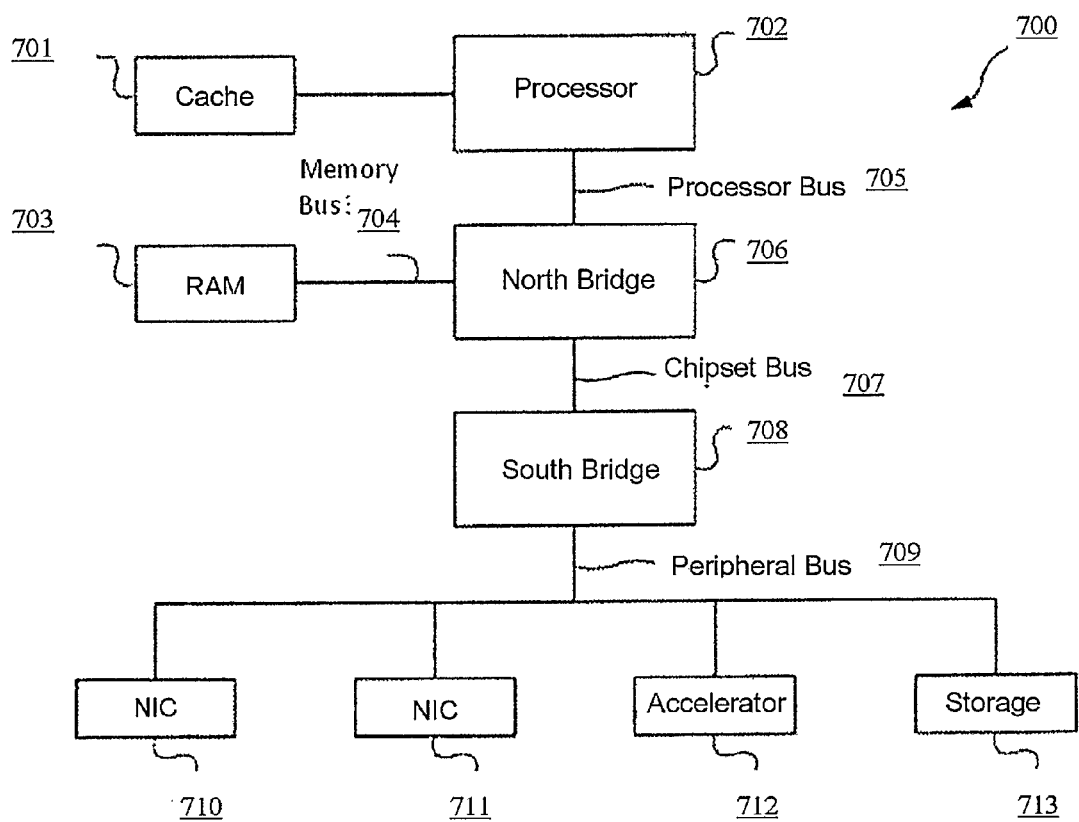
FIG. 7 is a block diagram illustrating a first example architecture of a computer system that can be used in connection with example embodiments of the present invention.

Various computer architectures are suitable for use with the invention. FIG. 7 is a block diagram illustrating a first example architecture of a computer system 700 that can be used in connection with example embodiments of the present invention. As depicted in FIG. 7, the example computer system can include a processor 702 for processing instructions. Non-limiting examples of processors include: Intel Core i7™ processor, Intel Core i5™ processor, Intel Core i3™ processor, Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, and/or personal data assistant devices.

Data Acquisition, Processing and Storage.

As illustrated in FIG. 7, a high speed cache 701 can be connected to, or incorporated in, the processor 702 to provide a high speed memory for instructions or data that have been recently, or are frequently, used by processor 702. The processor 702 is connected to a north bridge 706 by a processor bus 705. The north bridge 706 is connected to random access memory (RAM) 703 by a memory bus 704 and manages access to the RAM 703 by the processor 702. The north bridge 706 is also connected to a south bridge 708 by a chipset bus 707. The south bridge 708 is, in turn, connected to a peripheral bus 709. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 709. In some architectures, the functionality of the north bridge can be incorporated into the processor instead of using a separate north bridge chip.

In some embodiments, system 700 can include an accelerator card 712 attached to the peripheral bus 709. The accelerator can include field programmable gate arrays (FPGAs) or other hardware for accelerating certain processing.

Software Interface(s).

Software and data are stored in external storage 713 and can be loaded into RAM 703 and/or cache 701 for use by the processor. The system 700 includes an operating system for managing system resources; non-limiting examples of operating systems include: Linux, Windows™, MACOS™, BlackBerry OS™, iOS™, and other functionally-equivalent operating systems, as well as application software running on top of the operating system.

In this example, system 700 also includes network interface cards (NICs) 710 and 711 connected to the peripheral bus for providing network interfaces to external storage, such as Network Attached Storage (NAS) and other computer systems that can be used for distributed parallel processing.

Computer Systems.

Figure 8:
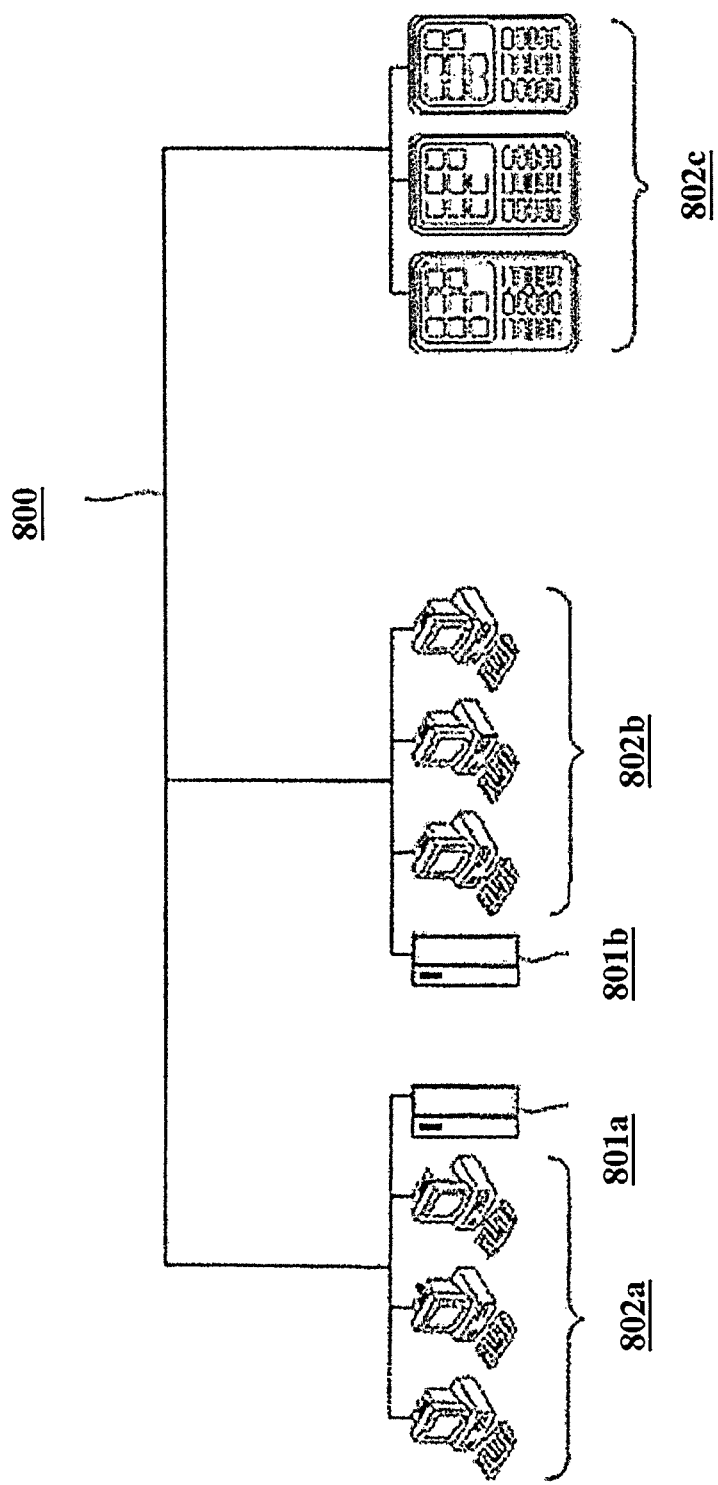
FIG. 8 is a diagram illustrating a computer network that can be used in connection with example embodiments of the present invention.

FIG. 8 is a diagram showing a network 800 with a plurality of computer systems 802a, and 802b, a plurality of cell phones and personal data assistants 802c, and Network Attached Storage (NAS) 801a, and 801b. In some embodiments, systems 802a, 802b, and 802c can manage data storage and optimize data access for data stored in Network Attached Storage (NAS) 801a and 802b. A mathematical model can be used for the data and be evaluated using distributed parallel processing across computer systems 802a, and 802b, and cell phone and personal data assistant systems 802c. Computer systems 802a, and 802b, and cell phone and personal data assistant systems 802c can also provide parallel processing for adaptive data restructuring of the data stored in Network Attached Storage (NAS) 801a and 801b. FIG. 8 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some embodiments, processors can maintain separate memory spaces and transmit data through network interfaces, back plane, or other connectors for parallel processing by other processors. In some embodiments, some or all of the processors can use a shared virtual address memory space.

Virtual Systems.

Figure 9:
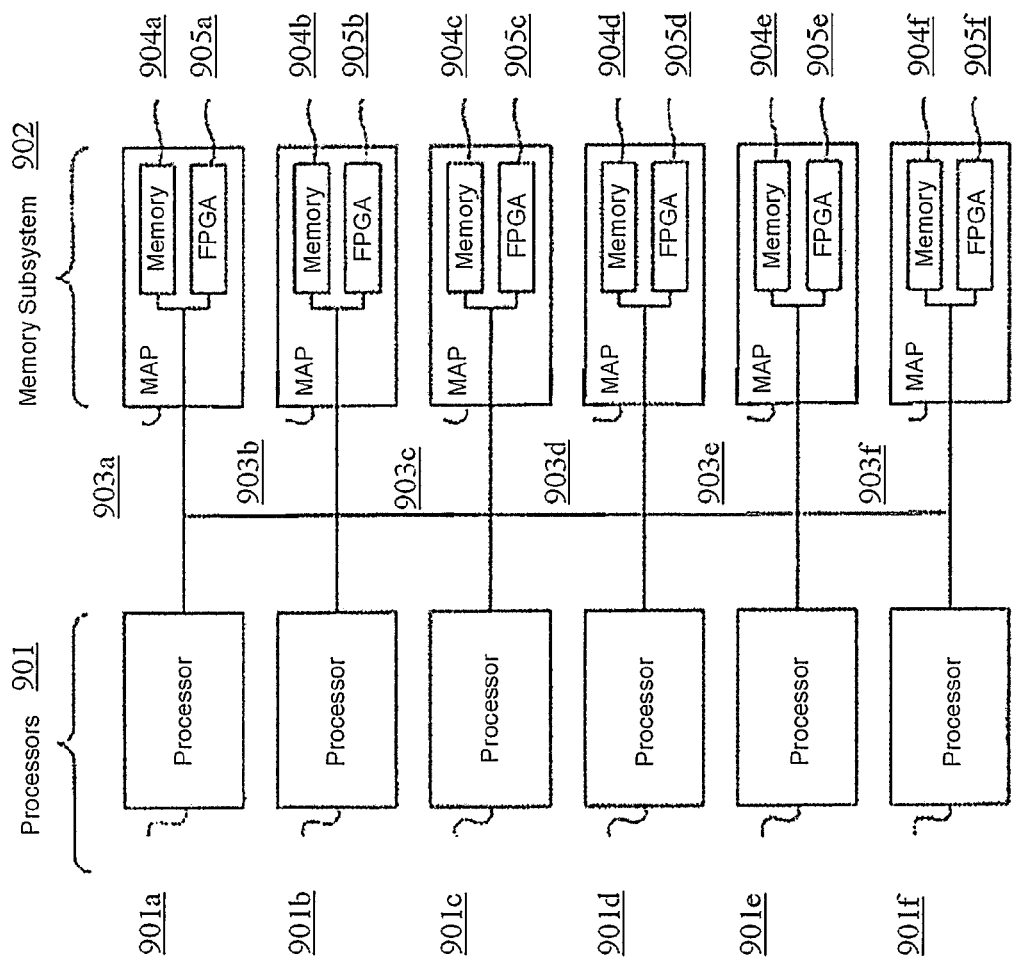
FIG. 9 is a block diagram illustrating a second example architecture of a computer system that can be used in connection with example embodiments of the present invention.

FIG. 9 is a block diagram of a multiprocessor computer system using a shared virtual address memory space. The system includes a plurality of processors 901a-f that can access a shared memory subsystem 902. The system incorporates a plurality of programmable hardware memory algorithm processors (MAPs) 903a-f in the memory subsystem 902. Each MAP 903a-f can comprise a memory 904a-f and one or more field programmable gate arrays (FPGAs) 905a-f. The MAP provides a configurable functional unit and particular algorithms or portions of algorithms can be provided to the FPGAs 905a-f for processing in close coordination with a respective processor. In this example, each MAP is globally accessible by all of the processors for these purposes. In one configuration, each MAP can use Direct Memory Access (DMA) to access an associated memory 904a-f, allowing it to execute tasks independently of, and asynchronously from, the respective microprocessor 901a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 9, system on chips (SOCs), application specific integrated circuits (ASICs), or other processing and logic elements. For example, the Set Processor and Optimizer can be implemented with hardware acceleration through the use of a hardware accelerator card, such as accelerator card 712 illustrated in FIG. 7.

Figure 10:
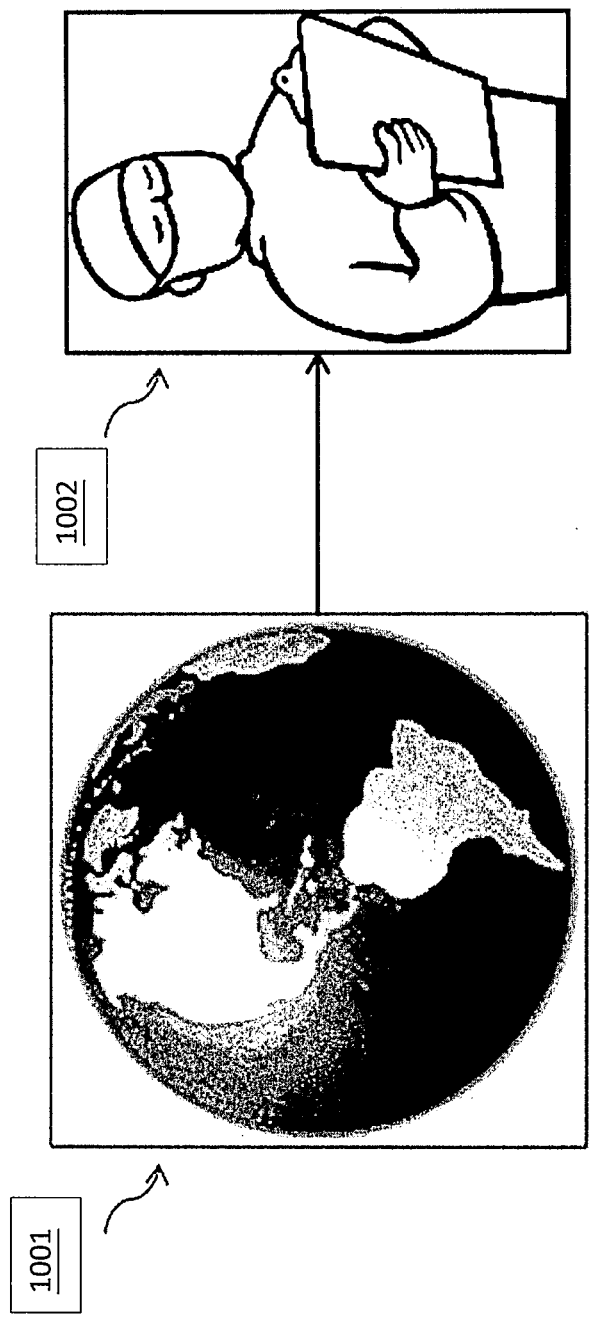
FIG. 10 illustrates a global network that can transmit a product of the invention.

Any embodiment of the invention described herein can be, for example, produced and transmitted by a user within the same geographical location. A product of the invention can be, for example, produced and/or transmitted from a geographic location in one country and a user of the invention can be present in a different country. In some embodiments, the data accessed by a system of the invention is a computer program product that can be transmitted from one of a plurality of geographic locations 1001 to a user 1002 (FIG. 10). Data generated by a computer program product of the invention can be transmitted back and forth among a plurality of geographic locations, for example, by a network, a secure network, an insecure network, an internet, or an intranet. In some embodiments, a system herein is encoded on a physical and tangible product.

Embodiments

Embodiment 1. A method comprising: a) contacting a device to an upper body portion of a subject, wherein the device comprises an accelerometer, a gyroscope, and a processor, wherein the subject is at elevated risk of developing ventilator-associated pneumonia; b) detecting by the accelerometer a change in posture of the subject; c) detecting by the gyroscope the change in posture of the subject; and d) calculating by the processor an angle formed by a cross sectional plane of the device and a plane of reference based on the detected change in posture of the subject.

Embodiment 2. The method of Embodiment 1, wherein the plane of reference is a plane of zero degree inclination.

Embodiment 3. The method of any one of Embodiments 1-2, wherein the upper body portion is the thorax of the subject.

Embodiment 4. The method of any one of Embodiments 1-2, wherein the upper body portion is a sternal surface of the subject.

Embodiment 5. The method of any one of Embodiments 1-4, wherein the accelerometer is a 3-axis accelerometer.

Embodiment 6. The method of any one of Embodiments 1-5, further comprising displaying the angle on a display.

Embodiment 7. The method of any one of Embodiments 1-6, wherein the accelerometer, the gyroscope, and the processor are in a common housing.

Embodiment 8. The method of any one of Embodiments 1-7, further comprising monitoring the angle and generating an alert when the angle is outside a predetermined range.

Embodiment 9. The method of Embodiment 8, wherein the predetermined range is from about 30 degrees to about 45 degrees.

Embodiment 10. The method of any one of Embodiments 1-9, wherein the contacting results in attachment of the device to the upper body portion of the subject.

Embodiment 11. The method of any one of Embodiments 1-10, wherein the contacting is to the subject's skin.

Embodiment 12. The method of any one of Embodiments 1-10, wherein the contacting is to a garment worn by the subject.

Embodiment 13. The method of any one of Embodiments 1-12, wherein the subject is bedridden.

Embodiment 14. The method of any one of Embodiments 1-13, wherein the subject is a patient in a hospital.

Embodiment 15. The method of any one of Embodiments 1-14, wherein the subject is a resident in a nursing home.

Embodiment 16. The method of any one of Embodiments 1-15, further comprising measuring a blood oxygenation of the subject.

Embodiment 17. The method of any one of Embodiments 1-16, further comprising measuring a heart rate of the subject.

Embodiment 18. The method of any one of Embodiments 1-17, further comprising measuring a breathing rate of the subject.

Embodiment 19. The method of any one of Embodiments 1-19, further comprising recording in a database the angle formed by the cross sectional plane of the device and the plane of reference.

Embodiment 20. The method of Embodiment 19, further comprising determining a history of postures of the subject over a period of time based on detected angles recorded in the database.

Embodiment 21. The method of any one of Embodiments 1-20, further comprising determining an upper body angle of the subject based on the angle formed by the cross sectional plane of the device and the plane of reference.

Embodiment 22. A device comprising: a) an attachment mechanism configured to attach the device to a subject who is at elevated risk of developing ventilator-associated pneumonia; b) an accelerometer configured to detect a change in posture of the subject; c) a gyroscope configured to detect the change in posture of the subject; and d) a processor configured to receive information from the accelerometer and the gyroscope, and determine an angle formed by a cross sectional plane of the device and a plane of reference based on the detected change in posture of the subject.

Embodiment 23. The device of Embodiment 22, wherein the plane of reference is a plane of zero degree inclination.

Embodiment 24. The device of any one of Embodiments 22-23, wherein the attachment mechanism is configured to attach to a sternal surface of the subject.

Embodiment 25. The device of any one of Embodiments 22-24, wherein the attachment mechanism is configured to attach to a garment of the subject.

Embodiment 26. The device of any one of Embodiments 22-25, wherein the accelerometer is a 3-axis accelerometer.

Embodiment 27. The device of any one of Embodiments 22-26, wherein the accelerometer, the gyroscope, and the processor are in a common housing.

Embodiment 28. The device of any one of Embodiments 22-27, wherein the angle formed by the cross sectional plane of the device and the plane of reference is an upper body angle of the subject.

Embodiment 29. The device of any one of Embodiments 22-28, further comprising a sensor configured to measure a magnetic field.

Embodiment 30. The device of any one of Embodiments 22-29, further comprising a sensor configured to measure a heart rate of the subject.

Embodiment 31. The device of any one of Embodiments 22-30, further comprising a sensor configured to measure a breathing rate of the subject.

Embodiment 32. The device of any one of Embodiments 22-31, further comprising a sensor configured to measure a blood oxygenation of the subject.

Embodiment 33. The device of any one of Embodiments 22-32, further comprising an alert system, wherein the alert system is configured to generate an alert when the angle formed by the cross sectional plane of the device and the plane reference is outside a predetermined range.

Embodiment 34. The device of Embodiment 33, wherein the predetermined range is from about 30 degrees to about 45 degrees.

Embodiment 35. The device of any one of Embodiments 22-34, further comprising a transmitter configured to transmit an output of the angle calculated by the processor.

Embodiment 36. The device of any one of Embodiments 22-35, further comprising a display configured to display an output of the angle calculated by the processor.

What is claimed is:

1. A method comprising:
    a) contacting a device to an upper body portion of a subject, wherein the device comprises an accelerometer, and a processor, wherein the subject is at elevated risk of developing ventilator-associated pneumonia;
    b) detecting by the accelerometer a change in posture of the subject;
    c) calculating by the processor an angle formed by a cross sectional plane of the device and a plane of reference based on the detected change in posture of the subject; and
    d) monitoring the angle formed by the cross sectional plane of the device and the plane of reference and generating an alert when the angle formed by the cross sectional plane of the device and the plane of reference is outside a predetermined range, wherein the predetermined range is from about 30 degrees to about 45 degrees, and wherein the subject is at elevated risk of developing ventilator-associated pneumonia when the angle formed by the cross sectional plane of the device and the plane of reference is outside the predetermined range.

2. The method of claim 1, further comprising recording in a database the angle formed by the cross sectional plane of the device and the plane of reference.

3. The method of claim 2, further comprising determining a history of postures of the subject over a period of time based on detected angles recorded in the database.

4. The method of claim 1, wherein the plane of reference is a plane of zero degree inclination.

5. The method of claim 1, wherein the upper body portion is the thorax of the subject.

6. The method of claim 1, wherein the upper body portion is a sternal surface of the subject.

7. The method of claim 1, wherein the accelerometer is a 3-axis accelerometer.

8. The method of claim 1, further comprising displaying the angle on a display.

9. The method of claim 1, wherein the accelerometer and the processor are in a common housing.

10. The method of claim 1, wherein the contacting results in attachment of the device to the upper body portion of the subject.

11. The method of claim 1, wherein the contacting is to the subject's skin.

12. The method of claim 1, wherein the contacting is to a garment worn by the subject.

13. The method of claim 1, wherein the subject is bedridden.

14. The method of claim 1, wherein the subject is a patient in a hospital.

15. The method of claim 1, wherein the subject is a resident in a nursing home.

16. The method of claim 1, further comprising measuring a blood oxygenation of the subject.

17. The method of claim 1, further comprising measuring a heart rate of the subject.

18. The method of claim 1, further comprising measuring a breathing rate of the subject.

19. The method of claim 1, further comprising determining an upper body angle of the subject based on the angle formed by the cross sectional plane of the device and the plane of reference.

20. The method of claim 1, further comprising changing the subject's posture to return the angle formed by the cross sectional plane of the device and the plane of reference to within the predetermined range.

21. The method of claim 1, further comprising maintaining the subject's posture in a position that keeps the angle formed by the cross sectional plane of the device and the plane of reference within the predetermined range.

22. A device comprising:
a) an attachment mechanism configured to attach the device to a subject who is at elevated risk of developing ventilator-associated pneumonia;
b) an accelerometer configured to detect a change in posture of the subject;
c) a processor configured to receive information from the accelerometer, and determine an angle formed by a cross sectional plane of the device and a plane of reference based on the detected change in posture of the subject; and
d) an alert system, wherein the alert system is configured to generate an alert when the angle formed by the cross sectional plane of the device and the plane of reference is outside a predetermined range, wherein the predetermined range is from about 30 degrees to about 45 degrees, wherein the subject is at elevated risk of developing ventilator-associated pneumonia when the angle formed by the cross sectional plane of the device and the plane of reference is outside the predetermined range.

23. The device of claim 22, wherein the plane of reference is a plane of zero degree inclination.

24. The device of claim 22, wherein the attachment mechanism is configured to attach to a sternal surface of the subject.

25. The device of claim 22, wherein the attachment mechanism is configured to attach to a garment of the subject.

26. The device of claim 22, wherein the accelerometer is a 3-axis accelerometer.

27. The device of claim 22, wherein the accelerometer and the processor are in a common housing.

28. The device of claim 22, wherein the angle formed by the cross sectional plane of the device and the plane of reference is an upper body angle of the subject.

29. The device of claim 22, further comprising a sensor configured to measure a magnetic field.

30. The device of claim 22, further comprising a sensor configured to measure a heart rate of the subject.

31. The device of claim 22, further comprising a sensor configured to measure a breathing rate of the subject.

32. The device of claim 22, further comprising a sensor configured to measure a blood oxygenation of the subject.

33. The device of claim 22, further comprising a transmitter configured to transmit an output of the angle calculated by the processor.

34. The device of claim 22, further comprising a display configured to display an output of the angle calculated by the processor.

* * * * *